United States Patent
Tseng

(10) Patent No.: US 11,608,312 B1
(45) Date of Patent: Mar. 21, 2023

(54) COMPOUND AND METHOD FOR PREPARATION OF LISDEXAMFETAMINE

(71) Applicant: SCI PHARMTECH INC., Taoyuan (TW)

(72) Inventor: Chih-Wei Tseng, Taoyuan (TW)

(73) Assignee: SCI PHARMTECH INC., Taoyuan (TW)

( * ) Notice: Subject to any disclaimer, the term of this patent is extended or adjusted under 35 U.S.C. 154(b) by 111 days.

(21) Appl. No.: 17/383,175

(22) Filed: Jul. 22, 2021

(51) Int. Cl.
  *C07C 231/12* (2006.01)
  *C07C 271/20* (2006.01)

(52) U.S. Cl.
  CPC .......... *C07C 231/12* (2013.01); *C07C 271/20* (2013.01); *C07C 2601/16* (2017.05)

(58) Field of Classification Search
  CPC .. C07C 231/12; C07C 271/20; C07C 2601/16
  See application file for complete search history.

(56) References Cited

U.S. PATENT DOCUMENTS

| | | |
|---|---|---|
| 2012/0157706 A1 | 6/2012 | Bauer et al. |
| 2016/0376618 A1 | 12/2016 | Goudriaan et al. |

FOREIGN PATENT DOCUMENTS

| | | | |
|---|---|---|---|
| WO | 2010042120 A1 | | 4/2010 |
| WO | 2010/148305 A1 | | 12/2010 |
| WO | WO2010/148305 | * | 12/2010 |
| WO | 2013011526 A1 | | 1/2013 |
| WO | 2017/098533 A2 | | 6/2017 |

* cited by examiner

*Primary Examiner* — Yevgeny Valenrod
*Assistant Examiner* — Blaine G Doletski
(74) *Attorney, Agent, or Firm* — Osha Bergman Watanabe & Burton LLP

(57) ABSTRACT

Provided is a compound represented by Formula (VI) for preparing lisdexamphetamine or a salt thereof. Also provided is a method for preparing lisdexamfetamine or a salt thereof including performing reduction and debenzylation of the compound represented by Formula (VI) by hydrogenation.

(VI)

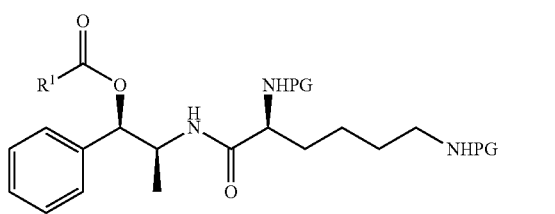

20 Claims, No Drawings

COMPOUND AND METHOD FOR PREPARATION OF LISDEXAMFETAMINE

BACKGROUND

1. Technical Field

The present disclosure relates to compounds for preparing lisdexamfetamine, and to methods for preparing lisdexamfetamine from the compounds.

2. Description of Associated Art

Lisdexamfetamine dimesylate, i.e., (2S)-2,6-diamino-N-[(1S)-1-methyl-2-phenylethyl] hexanamide dimethanesulfonate under the brand name of Vyvanse, is used to treat attention deficit hyperactivity disorder (ADHD) in adults and over 6-year-old children.

Also, it was approved to treat moderate to severe binge eating disorder (BED) by the US FDA in 2015. Lisdexamfetamine dimesylate increases attention and decreases restlessness in children and adults who are overactive, unable to concentrate for long periods of time, or easily distracted and impulsive. This medicament is usually used as apart of a total treatment program that includes social, educational, and psychological treatments.

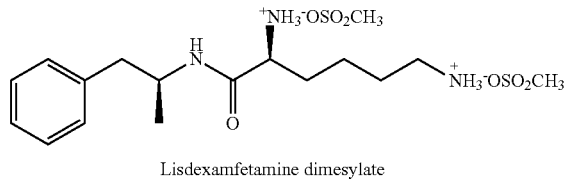

Lisdexamfetamine dimesylate

As to the preparation of lisdexamfetamine dimesylate, U.S. Patent Publication No. 2012/0157706 discloses a method for preparation of lisdexamfetamine dimesylate from D-amphetamine. The method involves reacting D-amphetamine with (S)-2,5-dioxopyrrolidin-1-yl 2,6-bis(benzyloxycarbonylamino) hexanoate to form a lysine amphetamine bearing benzylcarbamate protecting groups. The lysine amphetamine bearing the benzylcarbamate protecting groups is then converted to lisdexamfetamine dimesylate by catalytic hydrogenation to remove the benzylcarbamate protecting groups, followed by subsequent addition of methanesulfonic acid to generate the lisdexamfetamine dimesylate.

International Patent Publication No. WO 2010/042120 discloses a process for preparation of lisdexamfetamine by reacting D-amphetamine with (S)-2,6-bis((tert-butoxycarbonyl)amino)hexanoic acid in the presence of an alkylphosphonic acid anhydride (e.g., $T_3P$) as a coupling agent under a base condition including a solvent, followed by adding methanesulfonic acid to remove the tert-butoxycarbonyl protecting groups and thus generate lisdexamfetamine dimesylate. In addition, International Patent Publication No. WO 2013/011526 discloses another process for preparation of lisdexamfetamine by reacting D-amphetamine with (S)-2,6-bis((tert-butoxycarbonyl)amino)hexanoic acid in the presence of isobutyl chloroformate as a coupling agent under a base condition including a solvent.

International Patent Publication No. WO 2010/148305 discloses a process for preparation of lisdexamfetamine starting from L-norephedrine. First, L-norephedrine is converted to the corresponding chloro-D-amphetamine hydrochloride by thionyl chloride, and the resulting chloro-D-amphetamine hydrochloride is coupled with (S)-2,6-bis(2,2,2-trifluoroacetamido)hexanoic acid to obtain an N,N'-bis-trifluoroacetyl-protected chloro-lisdexamfetamine intermediate. Further, the N,N'-bis-trifluoroacetyl-protected chloro-lisdexamfetamine intermediate is converted to N,N'-bis-trifluoroacetyl-protected lisdexamfetamine by removal of chlorine with catalytic hydrogenation. Subsequently, lisdexamfetamine dimesylate is obtained by subjecting N,N'-bis-trifluoroacetyl-protected lisdexamfetamine to a hydrolysis reaction by methanesulfonic acid.

U.S. Patent Publication No. 2016/0376618 discloses a method for preparation of lisdexamfetamine from amfetamine, comprising reacting amfetamine with N,N'-bis-acyl-lysine ester and an enzyme catalyst to form a lisdexamfetamine stereoisomer, followed by converting the stereoisomer to lisdexamfetamine by treating with tetrakis(triphenylphosphine)palladium to remove an allyloxycarbonyl protecting group. Subsequently, by addition of methanesulfonic acid, lisdexamfetamine dimesylate is obtained.

International Patent Publication No. WO 2017/098533 discloses a process for preparation of lisdexamfetamine from (2S,3R)-2-methyl-3-phenylaziridine. In the disclosed process, (2S,3R)-2-methyl-3-phenylaziridine is coupled with Lys-2Boc-NHS to form a corresponding aziridine compound. The aziridine compound is then converted to N,N'-bis-Boc-protected lisdexamfetamine by ring-opening with catalytic hydrogenation, and further converted to lisdexamfetamine dimesylate by addition of methanesulfonic acid to decarboxylate the tert-butoxycarbonyl protecting groups.

The procedures described in above literatures mostly employ D-amphetamine as a starting material. D-amphetamine, also known as dextroamphetamine, is a Schedule II drug defined by the United States Controlled Substances Act. Therefore, special licenses, handling procedures, and compliance with governmental regulatory provisions are required for using large quantities of the controlled substance. As to other preparation processes, chloro-D-amphetamine or phenylaziridine is used as a starting material to replace the D-amphetamine. However, these processes involve additional steps of inserting a chloro group and thereafter removing the chloro group. In addition, multi-steps are required for synthesis of phenylaziridine.

Accordingly, there is still an unmet need for safe and effective methods and intermediates for preparing lisdexamfetamine and its pharmaceutically acceptable salts without using D-amphetamine as a starting material.

SUMMARY

The present disclosure provides a method for preparing lisdexamfetamine represented by Formula (I) below and a salt thereof:

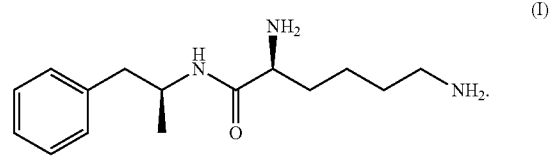 [SMILES: C[C@@H](Cc1ccccc1)NC(=O)[C@@H](N)CCCCN]

Also, the present disclosure provides a compound represented by Formula (VI) below or a salt thereof for preparing lisdexamphetamine or a salt thereof:

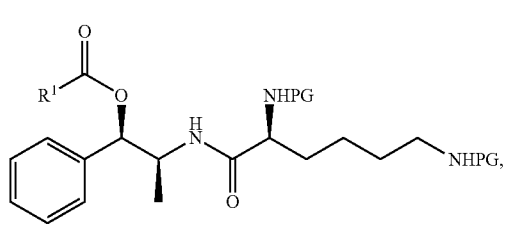

wherein $R^1$ is hydrogen, an aliphatic group, $C_1$-$C_6$ alkoxyl, a $C_1$-$C_6$ alkylamino group, or an aromatic group, and PG is an amine protecting group.

In at least one embodiment of the present disclosure, in the compound represented by Formula (VI), $R^1$ is methyl. In some embodiments, PG is benzyloxycarbonyl. In some embodiments, the compound for preparing lisdexamphetamine or a salt thereof is represented by Formula (VIa) below:

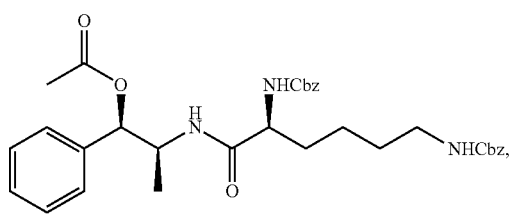

wherein Cbz refers to benzyloxycarbonyl.

In at least one embodiment of the present disclosure, the method for preparing lisdexamfetamine or a salt thereof provided herein comprises reducing an O-acylation group of an intermediate compound represented by Formula (VI) or a salt thereof through a catalytic hydrogenation to obtain the lisdexamphetamine or the salt thereof:

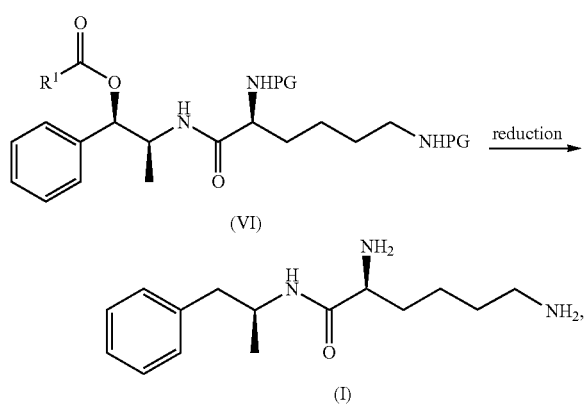

wherein $R^1$ is hydrogen, an aliphatic group, $C_1$-$C_6$ alkoxyl, a $C_1$-$C_6$ alkylamino group, or an aromatic group, and PG is an amine protecting group.

In at least one embodiment of the present disclosure, as illustrated below, the method further comprises reacting a compound represented by Formula (V) or a salt thereof with an acylation reagent to obtain the intermediate compound represented by Formula (VI):

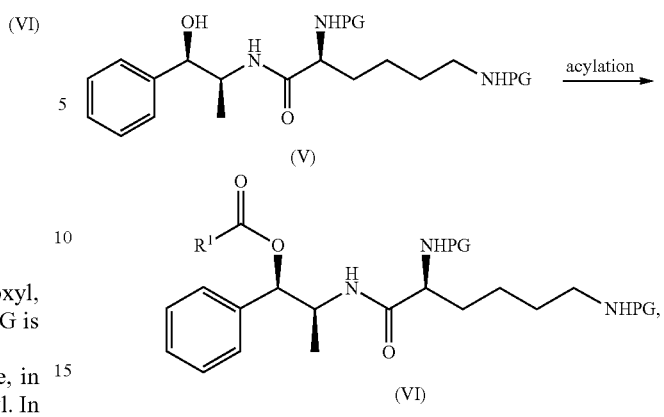

wherein $R^1$ and PG are defined as above.

In at least one embodiment of the present disclosure, as illustrated below, the method further comprises coupling L-norephedrine represented by Formula (II) or a salt thereof and a diamino protected L-lysine represented by Formula (IV) or a salt thereof to obtain the compound represented by Formula (V):

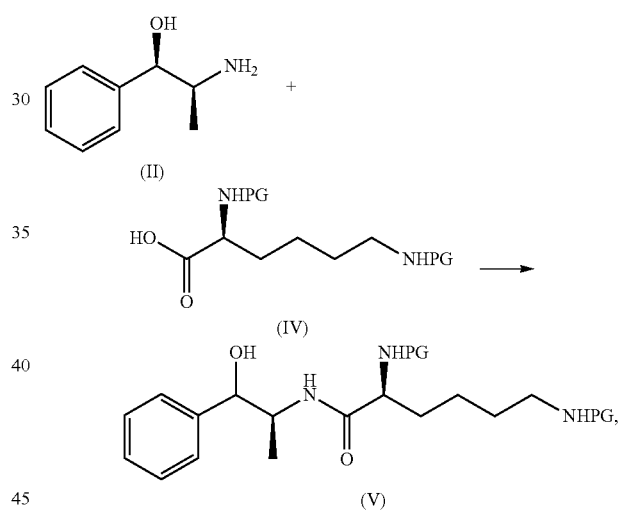

wherein PG is defined as above.

In some embodiments of the present disclosure, as illustrated below, the coupling L-norephedrine or the salt thereof and the diamino protected L-lysine or the salt thereof is carried out by reaction with an acid activating reagent:

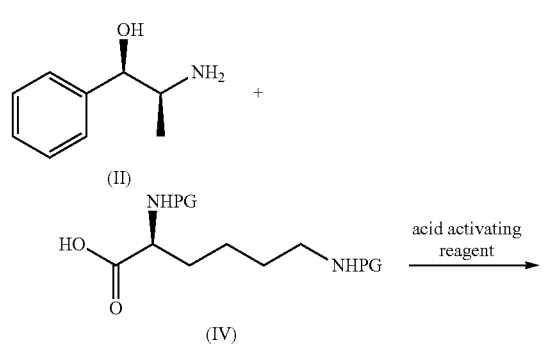

-continued

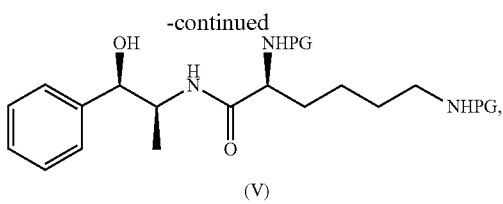

(V)

wherein PG is defined as above.

In at least one embodiment of the present disclosure, as illustrated below, the method further comprises reacting L-lysine represented by Formula (III) below with an amine protecting group in the presence of a protection reagent and a solvent to obtain the diamino protected L-lysine represented by Formula (IV):

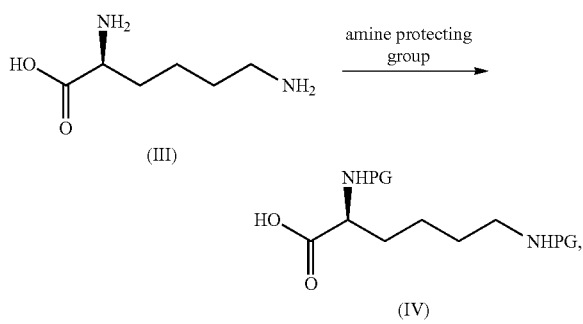

wherein PG is the amine protecting group.

In at least one embodiment of the present disclosure, the method further comprises contacting the lisdexamphetamine with methanesulfonic acid to obtain lisdexamfetamine dimesylate.

DETAILED DESCRIPTION OF THE EMBODIMENTS

The following examples are used to exemplify the present disclosure. A person of ordinary skill in the art can conceive the other advantages and effects of the present disclosure, based on the disclosure of the specification. The present disclosure can also be implemented or applied as described in different examples. It is possible to modify and/or alter the examples for carrying out this disclosure without contravening its scope, for different aspects and applications.

It is further noted that, as used in this disclosure, the singular forms "a," "an," and "the" include plural referents unless expressly and unequivocally limited to one referent. The term "or" is used interchangeably with the term "and/or" unless the context clearly indicates otherwise.

As used herein, the term "comprising" or "comprises" is used in reference to compositions, methods, and respective component(s) thereof, which are included in the present disclosure, yet open to the inclusion of unspecified elements. For example, a composition, mixture, process or method that comprises a list of elements or actions is not necessarily limited to only those elements or actions, but may include other elements or actions not expressly listed, or inherent to such composition, mixture, process, or method.

As used herein, the terms "first," "second," "third," and the like (if present) are used to distinguish similar objects and are not necessarily used to describe a particular order. It should be understood that the objects are interchangeable at an appropriate time.

As used herein, the term "about" generally means within 10%, 5%, 1%, or 0.5% of a given value or range. Alternatively, the term "about" means within an acceptable standard error of the mean when considered by one of ordinary skill in the art. Unless otherwise expressly specified, all of the numerical ranges, amounts, values and percentages such as those for quantities of materials, durations of time periods, temperatures, operating conditions, ratios of amounts, and the likes disclosed herein should be understood as modified in all instances by the term "about."

The present disclosure is directed to an intermediate compound and a method for preparing lisdexamphetamine or a salt thereof. In at least one embodiment of the present disclosure, the intermediate compound for the preparation method is represented by Formula (VI) below:

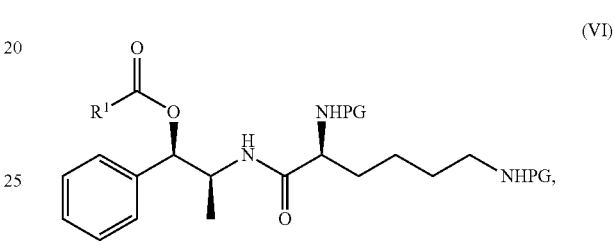

or a salt thereof, wherein $R^1$ is hydrogen, an aliphatic group, $C_1$-$C_6$ alkoxyl, a $C_1$-$C_6$ alkylamino group, or an aromatic group, and PG is an amine protecting group.

In at least one embodiment of the present disclosure, an exemplary process for preparing lisdexamfetamine dimesylate by the method provided herein is shown in Scheme 1 below:

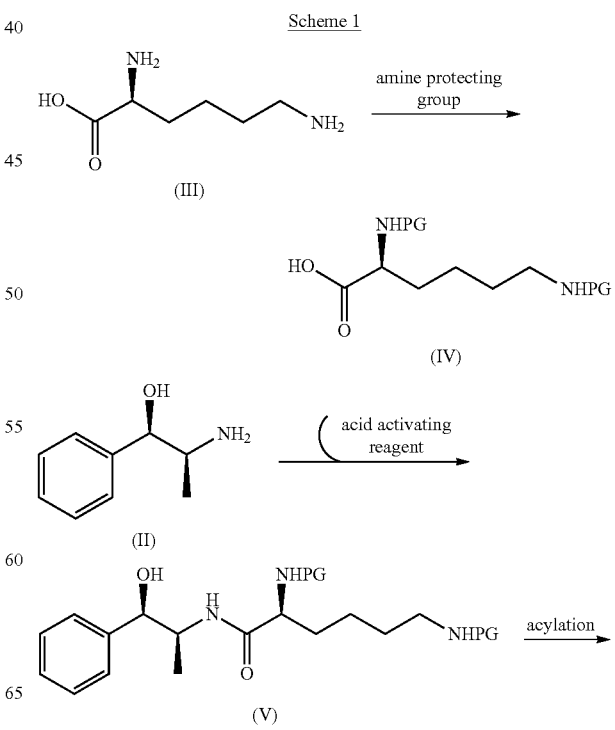

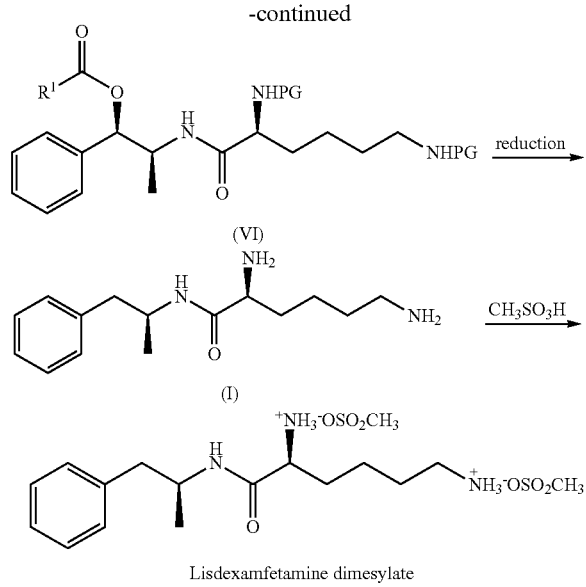

(VI)

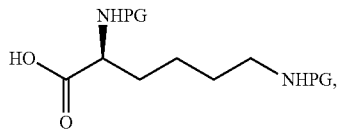

(I)

Lisdexamfetamine dimesylate

In the Scheme 1 illustrated above, $R^1$ is hydrogen, an aliphatic group, $C_1$-$C_6$ alkoxyl, a $C_1$-$C_6$ alkylamino, or an aromatic group, and PG is an amine protecting group.

In at least one embodiment of the present disclosure, the method for preparing lisdexamfetamine represented by Formula (I) and a salt thereof may start from preparation of a diamino protected L-lysine represented by Formula (IV):

(IV)

wherein PG is an amine protecting group.

In some embodiments, the diamino protected L-lysine represented by Formula (IV) is obtained by performing an amine protection of L-lysine monohydrochloride by using an amine protecting reagent in the presence of a suitable base and solvent.

In at least one embodiment of the present disclosure, the examples of the amine protecting group include, but are not limited to, t-butyloxycarbonyl (Boc), benzyloxycarbonyl (Cbz), allyloxycarbonyl (alloc), fluorenylmethyloxycarbonyl (Fmoc), trifluoroacetyl (TFA), acetyl (Ac), 2-(trimethylsilyl)ethoxycarbonyl (Teoc), tosyl (Ts), pivaloyl, and phthalimide. In some embodiments, the amino protecting group is benzyloxycarbonyl (Cbz), which may be from benzyl chloroformate as the amine protecting reagent.

In at least one embodiment of the present disclosure, the examples of the base for amine protection include, but are not limited to, N-methylmorpholine, diisopropylethyl amine (DIPEA), triethylamine (TEA), tri-n-propylamine, pyridine, alkaline metal hydroxides, and alkaline metal carbonates, such as sodium hydroxide, potassium hydroxide, calcium hydroxide, lithium hydroxide, sodium carbonate, potassium carbonate, calcium carbonate, sodium methoxide, potassium methoxide, sodium hydride, potassium hydride, and lithium hydride. In some embodiments, the base for amine protection is potassium hydroxide, potassium carbonate, or a combination thereof.

In at least one embodiment of the present disclosure, the examples of the solvent for amine protection include, but are not limited to, a polar protic solvent, such as methanol, ethanol, isopropyl alcohol, and water; or a polar aprotic solvent, such as dichloromethane, N-methylpyrrolidone, tetrahydrofuran, ethyl acetate, acetone, dimethylformamide, acetonitrile, and dimethyl sulfoxide; and a non-polar solvent, such as toluene, hexane, ether, and a mixture thereof. In some embodiments, the solvent for amine protection is water, methanol, or a combination thereof.

In at least one embodiment of the present disclosure, the reaction for preparing the diamino protected L-lysine represented by Formula (IV) may be carried out at a temperature of 0° C. to 60° C. for about 10 minutes to 24 hours. When using a benzyloxycarbonyl group as an amine protecting group, the reaction may be carried out at about 10° C. to 30° C. in the presence of a base. The completion of the reaction may be monitored by high pressure liquid chromatography or a suitable chromatographic technique. The diamino protected L-lysine represented by Formula (IV) may be isolated by any standard method known in the art. In some embodiments, the resulting diamino protected L-lysine is isolated by filtration.

In at least one embodiment of the present disclosure, the method for preparing lisdexamphetamine or a salt thereof comprises coupling the diamino protected L-lysine represented by Formula (IV) and L-norephedrine represented by Formula (II) to obtain a compound represented by Formula (V) as illustrated below:

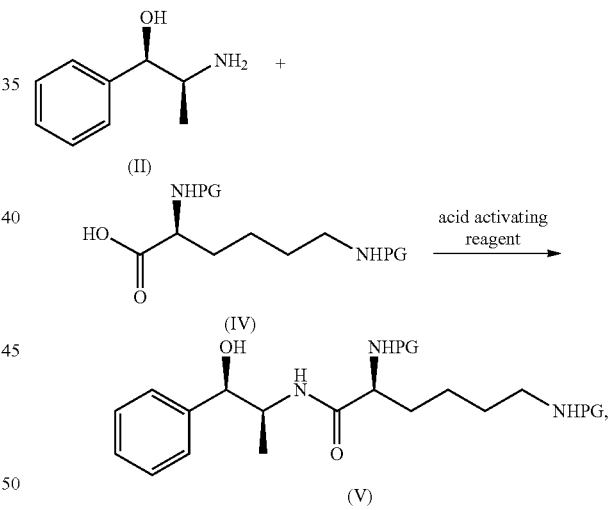

wherein PG is an amine protecting group.

In at least one embodiment of the present disclosure, the coupling comprising converting the diamino protected L-lysine represented by Formula (IV) to an active intermediate by using an acid activating reagent in the presence of a base and a solvent.

In at least one embodiment of the present disclosure, the examples of the acid activating reagent include, but are not limited to, dicyclohexyl carbodiimide (DCC), 1-ethyl-3-(dimethylamino)carbodiimide hydrochloride (EDC-HCl), carbonyldiimidazole (CDI), benzotriazol-1-yloxytri(pyrrolidino)phosphonium hexafluorophosphate (PyBOP), (1-[bis(dimethylamino)methylene]-1H-1,2,3-triazolo[4,5-b]pyridinium 3-oxide hexafluorophosphate (HATU), O-(1H-benzotriazol-1-yl)-N,N,N,N-tetramethyluronium hexafluorophosphate (HBTU), N-hydroxybenzotriazole, N-hydroxysuccinimide (HOSu), and haloformate, such as methyl chloroformate, ethyl chloroformate, isopropyl chloroformate, isobutyl chloroformate, benzyl chloroformate, phenyl chloroformate, and aryloxy chloroformate. In some embodiments, the acid activating reagent is isobutyl chloroformate.

In at least one embodiment of the present disclosure, the equivalent of isobutyl chloroformate as the acid activating reagent may be 0.95 to 1.05. In some embodiments, the equivalent of isobutyl chloroformate is about 0.96, about 0.97, about 0.98, about 0.99, about 1.0, about 1.01, about 1.02, about 1.03, or about 1.04.

In at least one embodiment of the present disclosure, the examples of the base for acid activation include, but are not limited to, N-methylmorpholine, diisopropylethyl amine (DIPEA), triethylamine (TEA), tri-n-propylamine, pyridine, and 1,8-diazabicyclo(5.4.0)undec-7-ene (DBU). In some embodiments, the base for acid activation is N-methylmorpholine.

In at least one embodiment of the present disclosure, the equivalent of N-methylmorpholine as the base for acid activation may be 1.0 to 2.4. In some embodiments, the equivalent of N-methylmorpholine is about 1.1, about 1.3, about 1.5, about 1.7, about 1.9, about 2.0, about 2.1, or about 2.3.

In at least one embodiment of the present disclosure, the examples of the solvent for acid activation include, but are not limited to, a polar aprotic solvent, such as dichloromethane, N-methylpyrrolidone, tetrahydrofuran, ethyl acetate, acetone, dimethylformamide, acetonitrile, and dimethyl sulfoxide. In some embodiments, the solvent for acid activation is dichloromethane.

In at least one embodiment of the present disclosure, the coupling may be carried out by reacting L-norephedrine represented by Formula (II) and the diamino protected L-lysine represented by Formula (IV) with an acid activating reagent at a temperature of from −20° C. to 40° C. for about 10 minutes to 24 hours. When using isobutyl chloroformate as an acid activating reagent, the reaction may be carried out at about −15° C. to 30° C., such as −15° C. to 15° C., −15° C. to 20° C., −10° C. to 30° C., and −5° C. to 25° C. The completion of the reaction may be monitored by high pressure liquid chromatography or a suitable chromatographic technique. The resulting compound represented by Formula (V) may be subjected to a subsequent step without further isolation.

In at least one embodiment of the present disclosure, the method for preparing lisdexamphetamine or a salt thereof comprises reacting the compound represented by Formula (V) with an acylation reagent to obtain the intermediate compound represented by Formula (VI) as illustrated below:

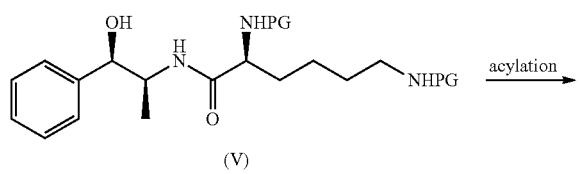

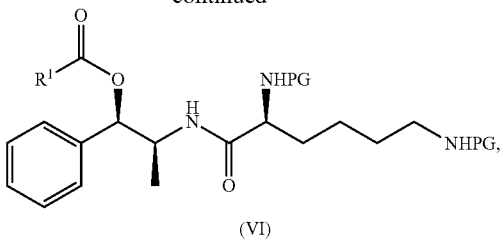

wherein PG is an amine protecting group.

In at least one embodiment of the present disclosure, the intermediate compound represented by Formula (VI) is obtained through converting the hydroxyl group of the compound represented by Formula (V) to an O-acylation group by using an acylation reagent and a base.

In at least one embodiment of the present disclosure, the O-acylation group may be O-formyl, O-acetyl, O-trifluoroacetyl, O-benzoyl, O-acrylyl, or O-carbonate group. In some embodiments, the examples of the acylation reagent include, but are not limited to, formic acid, methyl formate, ethyl formate, acetic acid, acetic anhydride, ethyl acetate, acetyl chloride, trifluoroacetic acid, trifluoroacetic anhydride, benzoic acid, benzoic anhydride, benzoic methyl ester, benzoic chloride, acrylic acid, acryloyl chloride, di-tert-butyl dicarbonate, and aryl chloroformate. In some embodiments, the acylation reagent is acetic anhydride.

In at least one embodiment of the present disclosure, the equivalent of acetic anhydride as the acylating reagent may be 1.0 to 3.0. In some embodiments, the equivalent of acetic anhydride is about 1.2, about 1.4, about 1.5, about 1.6, about 1.8, about 2.0, about 2.2, about 2.4, about 2.5, about 2.6, or about 2.8.

In at least one embodiment of the present disclosure, the examples of the base for acylation include, but are not limited to, imidazole, guanidine, N-methylmorpholine, diisopropylethyl amine (DIPEA), triethylamine (TEA), tri-n-propylamine, pyridine, 2,6-lutidine, piperidine, pyrrole, pyrrolidine, and 1,8-diazabicyclo(5.4.0)undec-7-ene (DBU). In some embodiments, the base for acylation is pyridine.

In at least one embodiment of the present disclosure, the equivalent of pyridine as the base for acylation may be 1.0 to 3.0. In some embodiments, the equivalent of pyridine is about 1.2, about 1.4, about 1.5, about 1.6, about 1.8, about 2.0, about 2.2, about 2.4, about 2.5, about 2.6, or about 2.8.

In at least one embodiment of the present disclosure, the acylation reaction may be carried out at a temperature of 25° C. to 100° C., such as 40° C. to 100° C., for about 10 minutes to 24 hours. When performing O-acetate reaction by acetic anhydride, the reaction may be carried out at about 60° C. to about 90° C. The completion of the reaction may be monitored by high pressure liquid chromatography or a suitable chromatographic technique. The intermediate compound represented by Formula (VI) may be isolated by any standard method known in the art. In some embodiments, the resulting intermediate compound is isolated by filtration.

In at least one embodiment of the present disclosure, the method for preparing lisdexamphetamine or a salt thereof comprises reducing the O-acylation group of the intermediate compound represented by Formula (VI) through a catalytic hydrogenation to obtain lisdexamphetamine represented by Formula (I) as illustrated below:

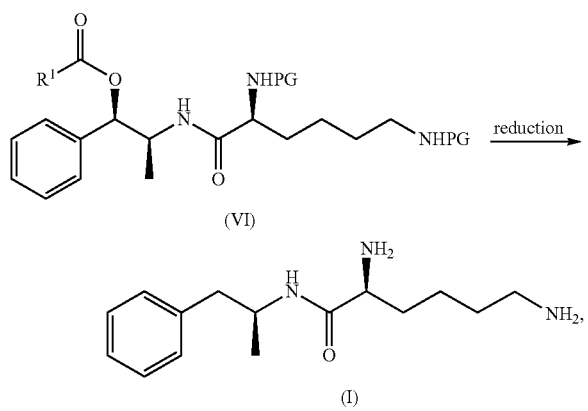

wherein PG is an amine protecting group.

In at least one embodiment of the present disclosure, the catalytic hydrogenation is carried out by contacting the intermediate compound represented by Formula (VI) by hydrogenation with a catalyst in the presence of a suitable solvent.

In at least one embodiment of the present disclosure, the catalyst for catalytic hydrogenation may be a transition metal catalyst, such as nickel, palladium, platinum, ruthenium, and rhodium. In some embodiments, the hydrogenation catalyst is Pd/C (palladium on charcoal).

In at least one embodiment of the present disclosure, the examples of the solvent for catalytic hydrogenation include, but are not limited to, a polar protic solvent, such as acetic acid, methanol, ethanol, isopropyl alcohol, and water; a polar aprotic solvent, such as dichloromethane, N-methylpyrrolidone, tetrahydrofuran, ethyl acetate, dimethylformamide, acetonitrile, and dimethyl sulfoxide; and a nonpolar solvent, such as toluene, hexane, ether, and any combination thereof. In some embodiments, the solvent for catalytic hydrogenation comprises methanol and water.

In at least one embodiment of the present disclosure, the weight ratio of the intermediate compound represented by Formula (VI) to the solvent for catalytic hydrogenation may be from 1:2 to 1:20. In some embodiments, the weight ratio of the intermediate compound represented by Formula (VI) to the solvent for catalytic hydrogenation is about 1:5, about 1:10, about 1:12, about 1:15, or about 1:18.

In at least one embodiment of the present disclosure, the reduction reaction may be carried out at a temperature of 25° C. to 80° C., such as 30° C. to 40° C., for about 1 hour to 24 hours. The completion of the reaction may be monitored by high pressure liquid chromatography or a suitable chromatographic technique.

In at least one embodiment of the present disclosure, the lisdexamphetamine represented by Formula (I) may be converted to its pharmaceutically acceptable salt by contacting with a corresponding acid thereof, such as methanesulfonic acid. In some embodiments, the pharmaceutically acceptable salt of lisdexamfetamine may be isolated by filtration.

Many examples have been used to illustrate the present disclosure. The examples below should not be taken as a limit to the scope of the present disclosure.

EXAMPLES

Example 1: Preparation of the Diamino Protected L-Lysine Represented by Formula (IV)

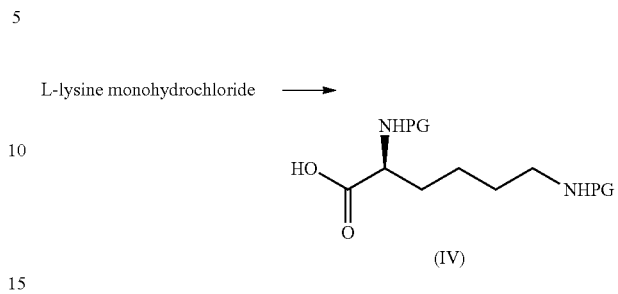

L-lysine monohydrochloride (91.3 g, 0.50 mole), potassium hydroxide (56.0 g, 0.50 mole), and potassium carbonate (152.0 g, 1.10 mole) were mixed in water (295.0 g) and methanol (500.0 g) at ambient temperature under inert atmosphere. The mixture was cooled to about 10° C., followed by adding benzyl chloroformate (187.6 g, 1.10 mole). After then, the reaction mixture was subjected to stirring at 25° C. for a half hour. The reaction mixture was then filtered at 25° C. and washed with methanol (230.0 g). The filtrate (1,273.0 g) was collected and concentrated at 60° C. to obtain a residual (764.0 g).

Further, the residual was extracted with toluene (250.0 g) and water (50.0 g). The toluene layer was separated from the aqua layer, and then washed with water (150.0 g). The toluene layer was abandoned, and the aqua layer was collected and acidified with 32% HCl (91.0 g, 0.80 mole). The acidified aqua was extracted with toluene (650.0 g), and then the toluene layer was separated from the aqua layer, and then washed twice with water (170.0 g and 100.0 g). The toluene layer was concentrated under reduced pressure at 60° C. to 80° C. to form a crude diamino protected L-lysine (232.1 g) (in which the protection group (PG) was a carbobenzoxy (Cbz) group) with purity of 91.5%, which was measured by ultra-performance liquid chromatography, and with reaction yield of 95.6%.

The crude diamino protected L-lysine was further isolated by crystallization with ethyl acetate (460.0 g) and heptane (920.0 g) and filtration. The wet cake of the diamino protected L-lysine represented by Formula (IV) (373.0 g) was obtained after filtration, and the dry cake (193.5 g) was obtained after drying. The obtained diamino protected L-lysine represented by Formula (IV) had purity of 98.2%, measured by ultra-performance liquid chromatography, and yield of 93%.

Example 2: Preparation of the Compound Represented by Formula (V)

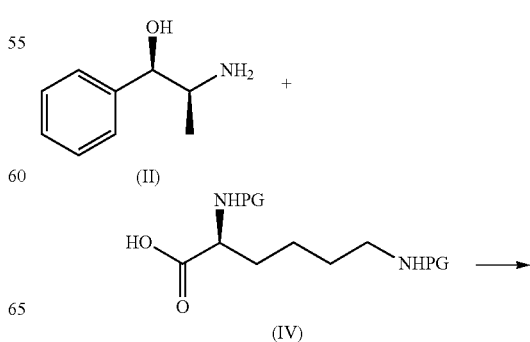

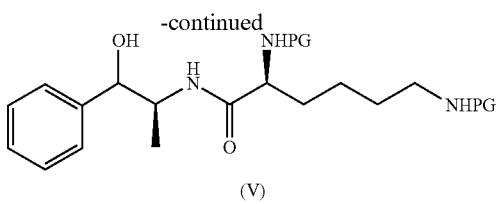

(V)

The diamino protected L-lysine represented by Formula (IV), in which the PG was a Cbz group (165.6 g, 0.40 mole) as prepared in Example 1, and isobutyl chloroformate (55.0 g, 0.404 mole) were mixed in dichloromethane (501.0 g) at ambient temperature under inert atmosphere. The mixture was cooled to about −15° C., followed by adding N-methylmorpholine (84.5 g, 0.84 mole). After addition of N-methylmorpholine, the reaction mixture was subjected to stirring at −10° C. to 0° C. for a half hour. L-norephedrine represented by Formula (II) (60.4 g, 0.40 mole) was dissolved in dichloromethane (300.0 g) and slowly mixed with the reaction mixture containing the diamino protected L-lysine represented by Formula (IV), isobutyl chloroformate, and N-methylmorpholine.

Further, the reaction mixture was subjected to stirring for 1 hour at 0° C. to 30° C., and then quenched with water (300.0 g). The dichloromethane layer was separated from the aqua layer, and then washed with 5% HCl (w/w) aqueous solution (100.0 g and 100.0 g) and water (100.0 g). The dichloromethane layer was collected and concentrated under reduced pressure at 60° C. to give a crude compound represented by Formula (V) (440.0 g) with the Cbz group as the PG.

The crude compound represented by Formula (V) was dissolved with AcOH (100.0 g) at 70° C. and concentrated to obtain 342 g of a residual with 93.3% of purity, measured by ultra-performance liquid chromatography. The residual of the compound represented by Formula (V) was used to a subsequent step without further purification.

Example 3: Preparation of the Compound Represented by Formula (VI)

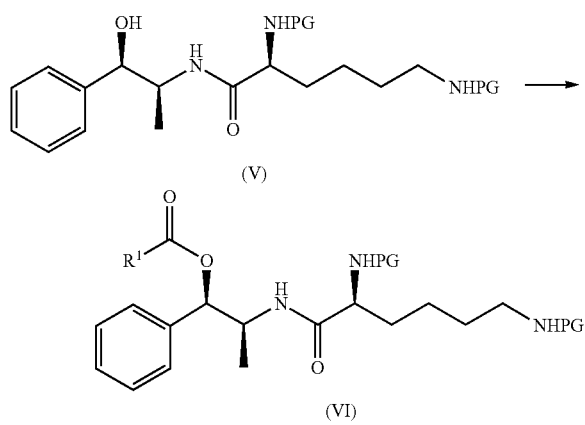

The compound represented by Formula (V) with the Cbz group as the PG as prepared in Example 2 (342.0 g) was mixed with acetic anhydride (62.0 g, 0.61 mole) and pyridine (49.0 g, 0.62 mole), followed by stirring at ambient temperature under inert atmosphere. The mixture was heated to about 80° C. to 90° C. and subjected to stirring for seven hours. After stirring for seven hours, the reaction mixture was concentrated under reduced pressure to obtain about 370 g of a residual.

Ethyl acetate (980.0 g) was added to the residual and heated (75° C.) to form a homogenous solution. The solution was cooled down slowly to about 1° C. to 2° C. and hold for another 2 hours. After filtration, the crude wet cake of the compound represented by Formula (VI) (325.0 g) (in which PG was the Cbz group and $R^1$ was methyl) was obtained with purity of 98.9% measured by ultra-performance liquid chromatography.

For recrystallization, the crude wet cake of the compound represented by Formula (VI) (325.0) was mixed in ethyl acetate (1,480.0 g) and heated to reflux (about 77° C.) to form a homogenous solution. The solution was cooled down slowly to about 1° C. to 2° C. and hold for another 2 hours. The wet cake of the compound represented by Formula (VI) (280.0 g) (in which PG was the Cbz group and $R^1$ was methyl) was obtained after filtration. After drying, the compound represented by Formula (VI) in white dry cake (170.0 g) was obtained with purity of 99.79%, measured by ultra-performance liquid chromatography, and yield of Formula (VIa)

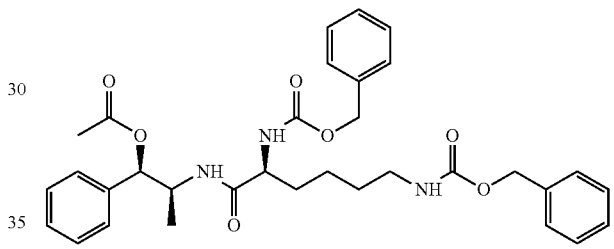

Chemical Formula: $C_{33}H_{39}N_3O_7$
Molecular Weight: 589.7

In an embodiment, the compound was represented by Formula (VIa) above: m.p.=166~167° C. IR (cm$^{-1}$) 3324 (br), 3288, 3089 (w), 3063 (w), 3033 (w), 2939, 2856, 1736, 1687, 1649, 1536, 1497, 1454, 1371, 1302, 1244, 1233, 1137, 1082, 1041, 977, 913, 754, 698. $^1$H NMR (600 MHz, DMSO-d$_6$) δ (ppm) 0.95 (d, 3H), 1.11-1.17 (m, 2H), 1.30-1.37 (m, 4H), 2.08 (s, 3H), 2.95 (dt, 2H), 3.91 (dt, 1H), 4.20 (m, 1H), 5.02 (s, 2H, 2H), 5.71 (d, 1H), 7.21 (t, 1H), 7.23 (d, 1H), 7.27-7.37 (Ar, 15H), 7.94 (d, 1H). $^{13}$C NMR (150 MHz, DMSO-d$_6$) δ (ppm) 15.00 (CH$_3$), 20.76 (CH$_3$), 22.47 (CH$_2$), 29.13 (CH$_2$), 31.54 (CH$_2$), 40.06 (CH$_2$), 47.83 (CH), 54.42 (CH), 65.13 (CH$_2$), 65.34 (CH$_2$), 76.33 (CH), 126.46 (CH), 127.12 (CH), 127.66 (CH), 127.72 (CH), 128.15 (CH), 128.32 (CH), 137.06 (C), 137.28 (C), 137.97 (C), 155.87 (C), 156.07 (C), 169.68 (C), 171.21 (C). MS (EI): m/z 590 (M)+.

The performance of the compound represented by Formula (VI) was determined by using ultra-performance liquid chromatography. The conditions of ultra-performance liquid chromatography assay were described in Table 1 below.

TABLE 1

| | |
|---|---|
| UV detector | Waters Model code UPL Serial # C15UPL 183A |
| Auto sampler | Waters Model code SDI Serial # C15SDI 107G |
| Pump | Waters Model code QSM Serial # C15QSM 379A |
| Column type | Waters ACQUITY UPLC BEH C8, 2.1(ID) × 50 mm, 1.7 μm |

TABLE 1-continued

| | |
|---|---|
| Detector | 220 nm |
| Column temperature | 35° C. |
| Sample temperature | 25° C. |
| Run time | 8 min |
| Dilute solvent | MeOH |
| Injection volume | 1 μL |

| UPLC Gradient Pump Program | |
|---|---|
| Mobile A | 1,000 mL water/50 mL acetonitrile/1 g TFA |
| Mobile B | Acetonitrile |

| Gradient | A % | B % | Flow rate |
|---|---|---|---|
| 0 min | 100 | 0 | 0.6 mL/min |
| 1 min | 100 | 0 | 0.6 mL/min |
| 6 min | 20 | 80 | 0.6 mL/min |
| 7 min | 0 | 100 | 0.8 mL/min |
| 7.1 min | 100 | 0 | 0.6 mL/min |
| 8 min | 100 | 0 | 0.6 mL/min |

Example 4: Preparation of Lisdexamphetamine from the Compound Represented by Formula

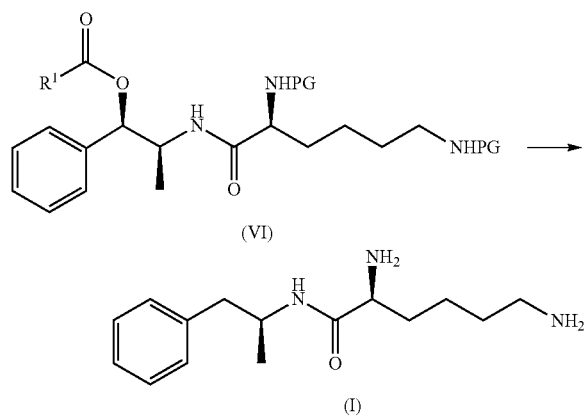

The compound represented by Formula (VI) with PG being the Cbz group and $R^1$ being methyl (10.0 g, 16.98 mole) as prepared in Example 3 was mixed with methanol (80.0 g) and water (20.0 g). 5% Palladium on charcoal (0.50 g) was added to the reaction mixture and kept under 0.4 to 0.5 MPa hydrogen pressure for 16 hours at 30° C. to 35° C. The completion of reaction was checked by liquid chromatography. Palladium on charcoal was filtered and washed with methanol and water combined solvent (20.0 g and 5.0 g, respectively). The reaction filtrate was then concentrated under reduced pressure at 50° C. to 80° C. The oily residual (4.5 g) of lisdexamfetamine represented by Formula (I) was obtained with purity of 99.2%, measured by ultra-performance liquid chromatography, and used to a subsequent step without further purification.

Example 5: Preparation of Lisdexamphetamine Dimesylate from Lisdexamphetamine

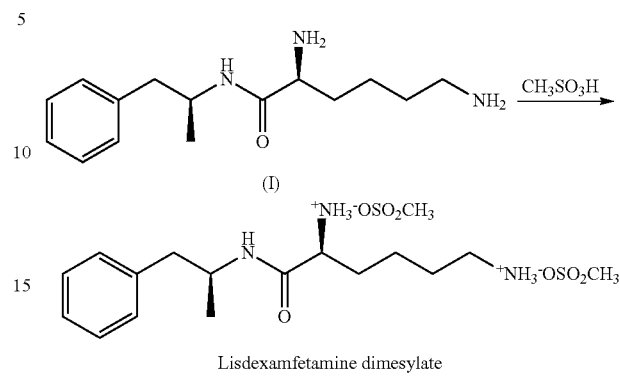

Lisdexamfetamine dimesylate

The oily compound represented by Formula (I) (4.5 g) as prepared in Example 4 was dissolved in isopropyl alcohol (45.0 g) and stirred at ambient temperature under inert atmosphere. To the reaction mixture, methanesulfonic acid (3.2 g) was slowly added. Further, the reaction mixture was heated to 55° C. to 65° C. and stirred for one hour. The reaction mixture was then cooled down slowly to room temperature (about 25° C.), stirred for 3 hours, filtered, washed with isopropyl alcohol (22.5 g) and dried under vacuum to obtain 5.5 g of lisdexamfetamine dimesylate with purity of 99.9%, measured by ultra-performance liquid chromatography.

Example 6: Preparation of L-Norephedrine from Propiophenone

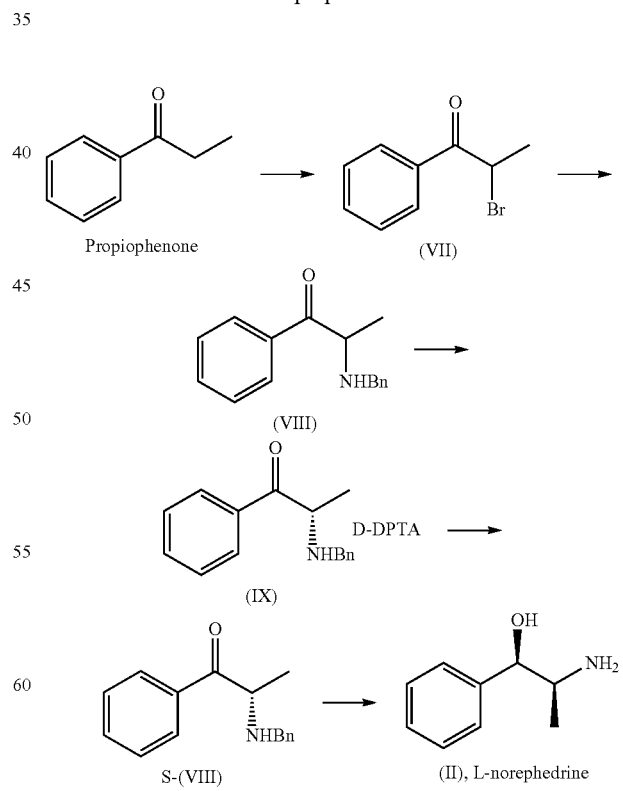

Propiophenone (268.0 g, 2.0 mole) was mixed with $Br_2$ (3.2 g, 0.02 mole) at 30° C. under inert atmosphere. Until the initial red color disappeared, N-bromosuccinimide (356.0 g, 2.0 mole) was added into the reaction mixture at the range of 35° C. to 45° C., and then acetic acid (26.8 g, 0.45 mole) was added. After adding, the reaction mixture was subjected to stirring at about 35° C. for one hour. The completion of reaction was checked by liquid chromatography. The reaction mixture was extracted with heptane (450.0 g) and water (870.0 g). The heptane layer was separated from the aqua layer, and washed twice with water (100.0 g and 100.0 g). The compound represented by Formula (VII) was produced in the heptane layer, and used for the next step without further purification.

Potassium carbonate (828.0 g, 6 eq) was dissolved in water (972.0 g) to form a clear solution (1,800.0 g), which was then mixed with benzyl amine (220.0 g, 2.05 mole). The BnNH$_2$/K$_2$CO$_3$/water mixture was cooled to about 10° C., followed by adding the compound represented by Formula (VII)/heptane layer. After adding, the reaction mixture was subjected to stirring at about 30° C. for 16 hours. The heptane layer was separated from the aqua layer, and washed twice with water (100.0 g and 100.0 g). The heptane layer was concentrated under reduced pressure at about 60° C. to obtain a residual (500.0 g) of a compound represented by Formula (VIII).

The residual (500.0 g) of Formula (VIII) was dissolved in methanol and isopropyl alcohol (250.0 g and 1000.0 g). (+)-O,O'-di-pivaloyl-D-tartaric acid (D-DPTA) (636.0 g, 2.0 mole) was added into the solution containing the compound of Formula (VIII). After adding, the reaction mixture was heated to about 60° C. for one hour and then cooled down slowly to room temperature (25° C.). The wet cake (1,143.0 g) of a compound represented by Formula (IX) was obtained after filtration, and the dry cake (946.0 g) was obtained after drying. The obtained compound represented by Formula (IX) had purity of 99.8%, measured by ultra-performance liquid chromatography, and yield of 85% (from propiophenone).

The compound represented by Formula (IX) (557.0 g, 1.0 mole) was mixed and stirred with heptane (795 g), water (1,295 g) and sodium hydroxide (80.0 g, 2.0 mole) at ambient temperature under inert atmosphere until all solid dissolved. The heptane layer was separated from the aqua layer, and washed with water (100.0 g). The S-form of the compound of Formula (VIII) was generated in the heptane layer, and then mixed with isopropyl alcohol (200.0 g). 5% Palladium on charcoal (10 g) was added to the reaction mixture and kept under 0.4 to 0.5 MPa hydrogen pressure for 4 hours at 30° C. to 35° C., and for 4 hours at 60° C. to 65° C. The completion of reaction was checked by liquid chromatography. Palladium on charcoal was filtered and washed with isopropyl alcohol (200.0 g). The reaction filtrate was then concentrated under reduced pressure at 50° C. to 80° C. The residual (138.5 g) of L-norephedrine was obtained with purity of 98.5% measured by ultra-performance liquid chromatography. The ratio of hydrogenated product ((1R,2S)-2-amino-1-phenyl-1-propanol:(1S,2S)-2-amino-1-phenyl-1-propanol) was 90:10. Yield of L-norephedrine from the compound of Formula (IX) was 91%.

Example 7: Preparation of L-Norephedrine from Phenylpropanolamine

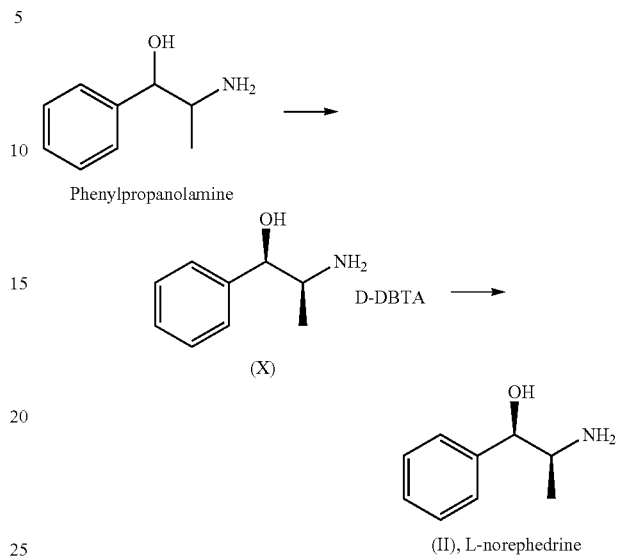

Phenylpropanolamine (PPA) (302.0 g, 2.0 mole) was mixed with isopropyl alcohol (IPA) (698.0 g) at 50° C. to form a clear solution under inert atmosphere. (+)-Dibenzoyl-D-tartaric acid (D-DBTA) (178.6 g, 0.48 mole) was dissolved in IPA (774.1 g) and slowly charged into PPA/IPA solution over three hours at 25° C. to 50° C. The solid was formed during charging. After charging, the reaction mixture was subjected to stirring at about 25° C. for two hours. After filtration, the crude wet cake (346.5 g) of the compound represented by Formula (X) was obtained with enantiomeric excess (e.e.) purity of about 95.7%, measured by chiral liquid chromatography.

For recrystallization, the crude wet cake of the compound represented by Formula (X) (346.5) was dissolved in methanol (1,200 g) and heated to reflux (about 66° C.) to distill out methanol (609.0 g) under inert atmosphere. The mixture solution was cooled down slowly to about 1° C. to 2° C. and hold for another two hours. The wet cake of the compound represented by Formula (X) was obtained after filtration, and the dry cake (258.5 g) of the compound represented by Formula (X) was obtained after drying (e.e. purity of about 99.99%, measured by chiral liquid chromatography).

The compound represented by Formula (X) (132.0 g, 0.4 mole) was mixed and stirred with cyclopentyl methyl ether (CPME) (250.0 g) and 2 M HCl$_{(aq)}$ (400.0 g) at 75° C. under inert atmosphere until all solid dissolved. The CPME layer was separated from the aqua layer, and washed with 1 M HCl$_{(aq)}$ (100.0 g). L-norephedrine of Formula (II) was generated in the collected HCl$_{(aq)}$ layer, and then neutralized with 45% NaOH (82.5 g. 0.93 mole) and extracted with dichloromethane four times (213.0 g, 103.0 g. 100.0 g and 100.0 g, respectively). The collected dichloromethane layer was concentrated under reduced pressure to obtain the residual (66.0 g) of L-norephedrine, in which the yield was 38.0%, from phenylpropanolamine.

While some of the embodiments of the present disclosure have been described in detail above, it is, however, possible for those of ordinary skill in the art to make various modifications and changes to the embodiments shown without substantially departing from the teaching and advantages of the present disclosure. Such modifications and changes are encompassed in the scope of the present disclosure as set forth in the appended claims.

What is claimed is:

1. A compound represented by Formula (VI) below or a salt thereof for preparing lisdexamphetamine or a salt thereof:

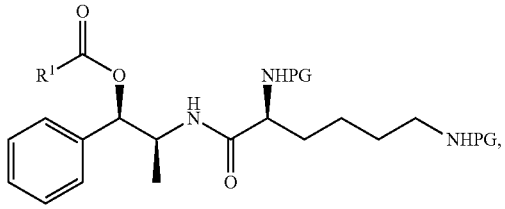

(VI)

wherein $R^1$ is hydrogen, an aliphatic group, $C_1$-$C_6$ alkoxyl, a $C_1$-$C_6$ alkylamino group, or an aromatic group, and PG is an amine protecting group.

2. The compound of claim 1, wherein $R^1$ is methyl and PG is benzyloxycarbonyl.

3. A method for preparing lisdexamphetamine or a salt thereof, comprising reducing an O-acylation group of an intermediate compound represented by Formula (VI) below or a salt thereof through a catalytic hydrogenation to obtain the lisdexamphetamine or the salt thereof:

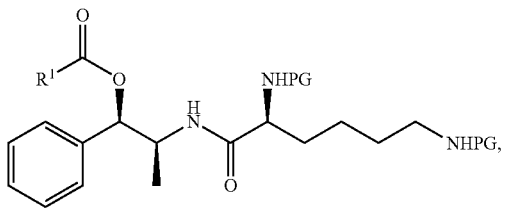

(VI)

wherein $R^1$ is hydrogen, an aliphatic group, $C_1$-$C_6$ alkoxyl, a $C_1$-$C_6$ alkylamino group, or an aromatic group, and PG is an amine protecting group.

4. The method of claim 3, wherein $R^1$ is methyl and PG is benzyloxycarbonyl.

5. The method of claim 3, wherein the catalytic hydrogenation is carried out by contacting the intermediate compound represented by Formula (VI) with a catalyst selected from the group consisting of palladium on charcoal, nickel, palladium, platinum, ruthenium, rhodium, and any combination thereof.

6. The method of claim 3, wherein the reducing is carried out in the presence of a first solvent at a first temperature in a range of from 25° C. to 80° C., and wherein the first solvent is selected from the group consisting of acetic acid, methanol, ethanol, isopropyl alcohol, water, dichloromethane, N-methylpyrrolidone, tetrahydrofuran, ethyl acetate, dimethylformamide, acetonitrile, dimethyl sulfoxide, toluene, hexane, ether, and any combination thereof.

7. The method of claim 6, wherein a weight ratio of the intermediate compound represented by Formula (VI) to the first solvent is from 1:2 to 1:20.

8. The method of claim 3, further comprising reacting a compound represented by Formula (V) below or a salt thereof with an acylation reagent to obtain the intermediate compound represented by Formula (VI):

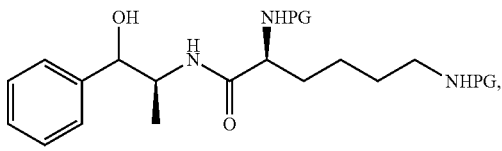

(V)

wherein PG is as defined in claim 3.

9. The method of claim 8, wherein the acylation reagent is selected from the group consisting of formic acid, methyl formate, ethyl formate, acetic acid, acetic anhydride, ethyl acetate, acetyl chloride, trifluoroacetic acid, trifluoroacetic anhydride, benzoic acid, benzoic anhydride, benzoic methyl ester, benzoic chloride, acrylic acid, acryloyl chloride, di-tert-butyl dicarbonate, aryl chloroformate, and any combination thereof.

10. The method of claim 9, wherein the acylation reagent is acetic anhydride having an equivalent of from 1.0 to 3.0.

11. The method of claim 8, wherein the reacting is carried out in the presence of a first base at a second temperature in a range of from 25° C. to 100° C., and wherein the first base is selected from the group consisting of imidazole, guanidine, N-methylmorpholine, diisopropylethyl amine (DIPEA), triethylamine (TEA), tri-n-propylamine, pyridine, 2,6-lutidine, piperidine, pyrrole, pyrrolidine, 1,8-diazabicyclo(5.4.0)undec-7-ene (DBU), and any combination thereof.

12. The method of claim 11, wherein the first base is pyridine having an equivalent of from 1.0 to 3.0.

13. The method of claim 8, further comprising coupling L-norephedrine represented by Formula (II) below or a salt thereof:

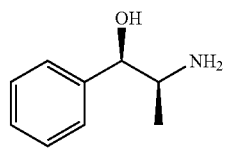

(II)

and
a diamino protected L-lysine represented by Formula (IV) below or a salt thereof:

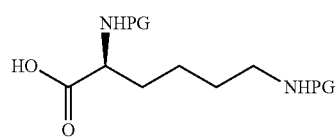

(IV)

to obtain the compound represented by Formula (V), wherein PG is as defined in claim 3.

14. The method of claim 13, wherein the coupling is carried out by reacting the L-norephedrine represented by Formula (II) or the salt thereof and the diamino protected L-lysine represented by Formula (IV) or the salt thereof with an acid activating reagent.

15. The method of claim 14, wherein the acid activating reagent is selected from the group consisting of dicyclohexyl carbodiimide (DCC), 1-ethyl-3-(dimethylamino)carbodiimide hydrochloride (EDC-HCl), carbonyldiimidazole (CDI), benzotriazol-1-yloxytri(pyrrolidino)phosphonium hexafluorophosphate (PyBOP), (1-[bis(dimethylamino)methylene]-1H-1,2,3-triazolo[4,5-b]pyridinium 3-oxide hexafluorophosphate (HATU), O-(1H-benzotriazol-1-yl)-N,N,N,N-tetramethyluronium hexafluorophosphate (HBTU), N-hydroxybenzotriazole, N-hydroxysuccinimide (HOSu), methyl chloroformate, ethyl chloroformate, isopropyl chloroformate, isobutyl chloroformate, benzyl chloroformate, phenyl chloroformate, aryloxy chloroformate, and any combination thereof.

16. The method of claim 15, wherein the acid activating reagent is isobutyl chloroformate having an equivalent of from 0.95 to 1.05.

17. The method of claim 14, wherein the coupling is carried out in the presence of a second base and a second solvent at a third temperature in a range of from −20° C. to 40° C.

18. The method of claim 17, wherein the second solvent is selected from the group consisting of dichloromethane, N-methylpyrrolidone, tetrahydrofuran, ethyl acetate, acetone, dimethylformamide, acetonitrile, dimethyl sulfoxide, and any combination thereof, and the second base is selected from the group consisting of N-methylmorpholine, diisopropylethyl amine (DIPEA), triethylamine (TEA), tri-n-propylamine, pyridine, 1,8-diazabicyclo(5.4.0)undec-7-ene (DBU), and any combination thereof.

19. The method of claim 18, wherein the second base is N-methylmorpholine having an equivalent of from 1.0 to 2.4.

20. The method of claim 3, further comprising contacting the lisdexamphetamine with methanesulfonic acid to obtain lisdexamfetamine dimesylate.

\* \* \* \* \*